(12) United States Patent
Sugiyama et al.

(10) Patent No.: US 9,861,322 B2
(45) Date of Patent: Jan. 9, 2018

(54) MEASUREMENT DATA MONITOR FOR MEDICAL EQUIPMENT AND MEASUREMENT DATA MONITORING SYSTEM FOR MEDICAL EQUIPMENT

(71) Applicant: NIHON KOHDEN CORPORATION, Tokyo (JP)

(72) Inventors: Kumi Sugiyama, Tokyo (JP); Masami Tanishima, Tokyo (JP); Teiji Ukawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 122 days.

(21) Appl. No.: 14/195,470

(22) Filed: Mar. 3, 2014

(65) Prior Publication Data

US 2014/0266786 A1    Sep. 18, 2014

(30) Foreign Application Priority Data

Mar. 12, 2013    (JP) .................................. 2013-048665

(51) Int. Cl.
*A61B 5/00* (2006.01)
*G06F 19/00* (2011.01)

(52) U.S. Cl.
CPC .............. *A61B 5/746* (2013.01); *A61B 5/742* (2013.01); *G06F 19/3406* (2013.01); *G06F 19/3487* (2013.01)

(58) Field of Classification Search
CPC ..... A61B 5/742; A61B 5/746; A61B 5/02455; A61B 5/02055; A61B 5/7435; A61B 5/002; G06F 19/3406; G06F 19/3487; G06F 19/3418; A61N 1/37258
USPC ..... 340/870.4, 500, 501, 573.1, 539.12, 3.1, 340/3.9; 600/301, 300, 306, 323, 346; 345/440
See application file for complete search history.

(56) References Cited

U.S. PATENT DOCUMENTS

| 5,865,736 A | 2/1999 | Baker, Jr. et al. |
| 6,569,095 B2 * | 5/2003 | Eggers ..................... A61B 5/00 128/903 |
| 2004/0122297 A1 * | 6/2004 | Stahmann .......... A61B 5/02055 600/300 |

(Continued)

FOREIGN PATENT DOCUMENTS

| CN | 1678238 A | 10/2005 |
| CN | 101248984 A | 8/2008 |

(Continued)

OTHER PUBLICATIONS

The extended European Search Report for the related European Patent Application No. 14157706.4 dated Jul. 29, 2014.
Notification of First Office Action issued in Chinese Patent Application No. 201410079055.6 dated Jun. 2, 2016.
Notification of Reasons for Refusal issued in Japanese Patent Application No. 2013-048665 dated May 10, 2016.

*Primary Examiner* — Mirza Alam
(74) *Attorney, Agent, or Firm* — Pearne & Gordon LLP (57) ABSTRACT

A measurement data monitor of the presently disclosed subject matter has a display section for displaying measurement data measured by a medical device; and a display control section for causing the display section to display measurement data, wherein the measurement data displayed on the display section include elements; that is, a measurement value of measurement data and duration of the measurement value.

11 Claims, 8 Drawing Sheets

(56) References Cited

U.S. PATENT DOCUMENTS

| | | | |
|---|---|---|---|
| 2004/0249249 A1* | 12/2004 | Lawson | A61B 5/02405 600/300 |
| 2006/0074321 A1 | 4/2006 | Kouchi | |
| 2008/0208480 A1 | 8/2008 | Kuriyama | |
| 2009/0054743 A1* | 2/2009 | Stewart | G06T 11/206 600/301 |
| 2010/0324377 A1* | 12/2010 | Woehrle | A61B 5/021 600/300 |
| 2011/0105854 A1* | 5/2011 | Kiani | G06F 19/327 600/300 |
| 2012/0265040 A1 | 10/2012 | Ito | |
| 2013/0006151 A1 | 1/2013 | Main | |
| 2013/0044111 A1* | 2/2013 | VanGilder | A61B 5/044 345/440 |

FOREIGN PATENT DOCUMENTS

| | | |
|---|---|---|
| JP | 2010-194306 A | 9/2010 |
| JP | 2011-509731 A | 3/2011 |
| JP | 2011-145932 A | 7/2011 |
| JP | 2011-147493 A | 8/2011 |
| JP | 4553406 B2 | 3/2012 |
| JP | 2012-217724 | 11/2012 |
| WO | 2011/091517 A1 | 8/2011 |
| WO | 2012/158720 A1 | 11/2012 |

\* cited by examiner

MEASUREMENT DATA MONITOR FOR MEDICAL EQUIPMENT AND MEASUREMENT DATA MONITORING SYSTEM FOR MEDICAL EQUIPMENT

CROSS-REFERENCE TO RELATED APPLICATIONS

This application claims the benefit of Japanese Patent Application No. 2013-048665 (filed on Mar. 12, 2013), the entire contents of which are hereby incorporated by reference.

BACKGROUND

The presently disclosed subject matter relates to a measurement data monitor for medical equipment and a measurement data monitoring system for medical equipment that determine a medical condition of a patient and set setup threshold line of physiological parameter which serve as criteria for determining activation of an alarm.

A heretofore-proposed physiological parameter measurement device is configured such that threshold values used for determining whether or not a measurement value of physiological parameter to be measured is abnormal is previously set and that an alarm is activated when a measurement value has exceeded the threshold value.

However, when only an excess of a measurement value over a threshold value is taken as a criterion for activating an alarm, an alarm is frequently activated by a measurement error attributable to noise or signal artifact or variations in measurement value attributable to temporary physiological fluctuations. In many cases, activation of such an alarm is unwanted from a clinical viewpoint, which often becomes burdensome for healthcare personnel.

Accordingly, in order to diminish frequent activation of an unwanted alarm, Japanese Patent No. 4553406 discloses a method and apparatus for reducing an unwanted alarm. Specifically, the measurement value exceeded the threshold value are integrated over its duration. When an integration result exceeds a predetermined value, an alarm is activated.

A published Japanese translation of a PCT patent application, JP-T-2011-509731, discloses an alarm control method. The term JP-T means. Under the method, consideration is given to an extent to which a threshold value is exceeded. When an extent to which the predetermined threshold value is exceeded is small, a long alarm delay period is set. Conversely, when the extent to which the threshold value is exceeded is large, a short alarm delay period is set. A period during which a measurement value exceeded the threshold value exceeds the alarm delay periods set for the respective extents, an alarm is activated.

However, in relation to the method and apparatus for reducing an unwanted alarm described in connection with Japanese Patent No. 4553406, the previously-set predetermined integral is not necessarily suitable for an individual patient.

Further, under the alarm control method described in connection with International Publication No. JP-T-2011-509731, the alarm delay period set for each of the extents to which the threshold value is exceeded is not always said as delay periods suitable for the current state of the patient.

When setting conditions for activating an alarm, the healthcare personnel encounters a limit on providing more preferable settings for all patients because the patients individually differ in terms of a medical condition. In particular, in relation to threshold values of physiological parameter, there is a tendency toward setting a threshold value that secures higher safety. For these reasons, it is difficult to set optimum conditions for all the patients because of anxiety that safety might not be assured.

SUMMARY

The presently disclosed subject matter provides a measurement data monitor for medical equipment and a measurement data monitoring system for medical equipment that make it possible to perform a more appropriate determination and conduct settings for patients who each have different conditions, in connection with a determination about a medical condition of a patient and setting of threshold points of measurement data measured by medical equipment.

It is therefore an aspect of the presently disclosed subject matter to provide a measurement data monitor for medical equipment comprising:

a display section configured to display measurement data measured by medical equipment;

a display control section configured to cause the display section to display the measurement data, wherein the measurement data displayed on the display section include calculated measurement values that contain elements of the measurement data and durations of the respective measurement values.

In the measurement data monitor, the measurement data displayed on the display section may include calculated measurement values that were measured in the past.

In the measurement data monitor, the display control section may cause the display section to display a screen which displays the calculated measurement values on two-dimensional coordinate.

In the measurement data monitor, the display control section may cause the display section to display a threshold setup screen that is used for setting on two-dimensional coordinates setup threshold points of the measurement data that are to serve as criteria for determining activation of an alarm.

In the measurement data monitor, the calculated measurement values may be displayed as two-dimensional coordinate data on the threshold setup screen at the time of setting of the setup threshold points. On the threshold setup screen, threshold points each of which include two elements composed of a threshold value for the measurement data and duration (delay time) of the measurement data may be displayed to form the threshold line.

In the measurement data monitor, the threshold line may be formed from at least two setup threshold points.

In the measurement data monitor, the display section may display at least one of a trend graph and a histogram of relevant measurement data.

In the measurement data monitor, the display section may display measurement data, alarm activation data that are caused by existing setup threshold value set with regard to the measurement data, and alarm activation simulation data that are simulated to be caused by setup threshold points changed and set with regard to the measurement data.

In the measurement data monitor, dots to be plotted on the graph may be categorized according to a predetermined standard, and plotted dots conforming to the standard are displayed in different forms.

In the measurement data monitor, one of dots plotted on the graph where the calculated measurement values are displayed is selected, whereby relevant data near a point in time when the plotted dot was measured may be displayed.

According to another aspect of the presently disclosed subject matter, there is provided a measurement data monitor comprising:

a display section; and a display control section configured to control the display section, wherein the display control section causes the display section to display a threshold setup screen that is used for setting setup threshold points used as criteria for determining activation of an alarm in a format which is specified by a measurement value of measurement data measured by medical equipment and a delay time of the measurement value.

According to still another aspect of the presently disclosed subject matter, there is provided a measurement data monitoring system for medical equipment that includes a plurality of measurement data monitors for medical equipment and a central monitor which manages the monitors in a centralized manner and which is connected to the monitors via a network, and that is operable to display calculated measurement values of various parameters acquired by the respective measurement data monitors on the central monitor via the network, wherein calculated measurement values of a plurality of patients are plotted and displayed, while being overlaid, on the central monitor.

BRIEF DESCRIPTION OF THE DRAWINGS

FIGS. 6A and 6B are graphs illustrating procedures for calculating past measurement values of $SpO_2$, wherein

DETAILED DESCRIPTION OF EMBODIMENTS

An embodiment of a measurement data monitor of the presently disclosed subject matter is hereunder described by reference to the accompanying drawings.

Figure 1:
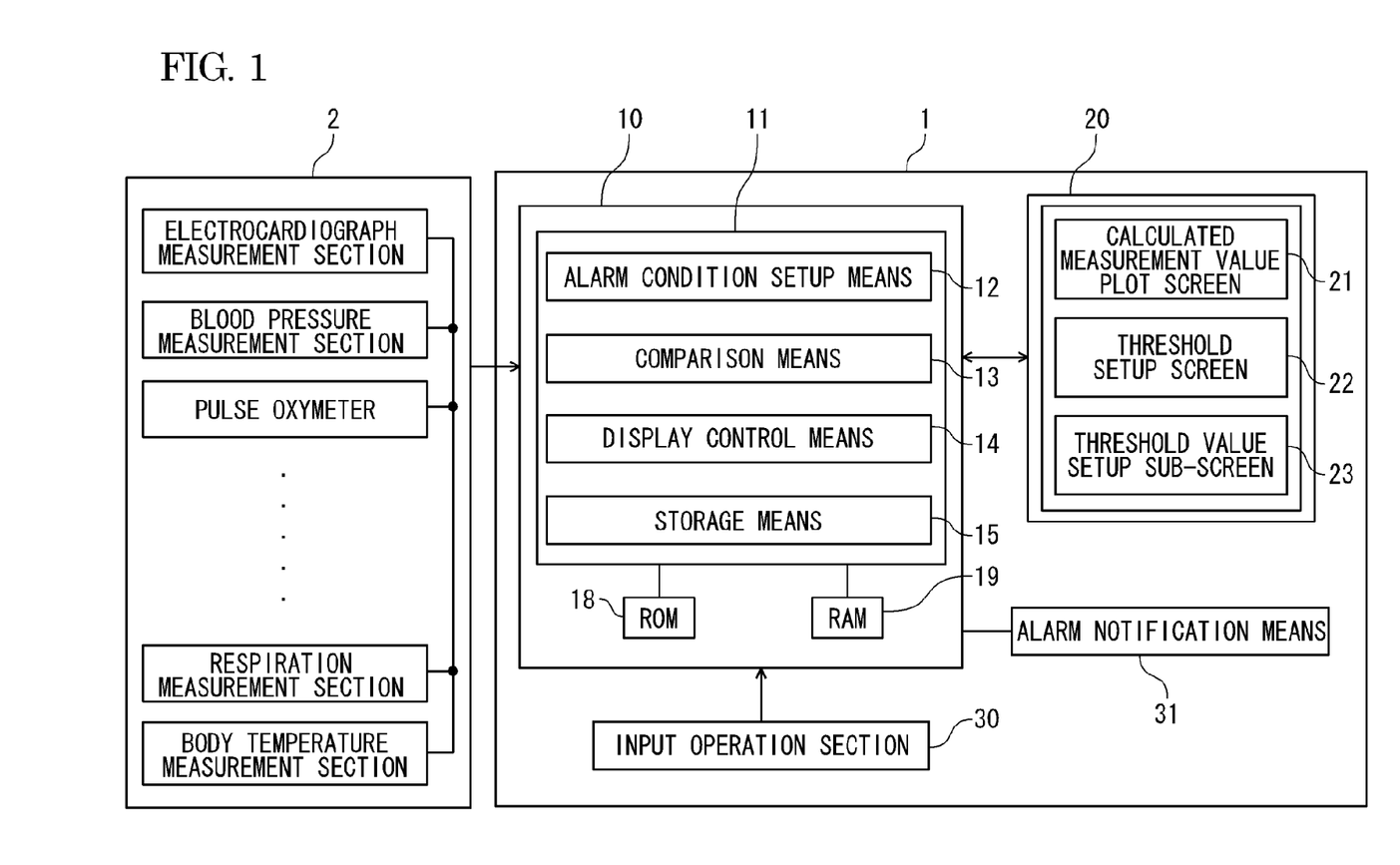
FIG. 1 is a block diagram illustrating a configuration of a measurement data monitor of the presently disclosed subject matter.

FIG. 1 illustrates a measurement data monitor 1 for medical equipment. The measurement data monitor 1 is described as an apparatus used for each patient; namely, a so-called bedside monitor, in the embodiment. However, the measurement data monitor can also be a central monitor.

The measurement data monitor 1 is connected to measurement data acquisition unit 2. In addition to acquiring physiological parameter, such as a heart rate (pulse rate), a value of blood pressure, $SpO_2$ (oxygen saturation), an inspired oxygen concentration, respiration, a body temperature, the measurement data acquisition unit 2 acquires measurement data including information, like an integrated drug dosage and an anesthetic depth. Devices (sensor), such as an electrocardiograph built in an electrocardiograph measurement section, a sphygmomanometer outfitted to a sphygmomanometry section, and a pulse oximeter, can be mentioned as the specific measurement data acquisition unit 2. A patient wears the measurement data acquisition unit 2, and measurement data acquired by the measurement data acquisition unit 2 are input to the measurement data monitor 1. In this regard, the measurement data can be input to the measurement data monitor 1 (a bedside monitor, a central monitor, and the like) by means of either wired or wireless transmission.

The measurement data monitor 1 comprises a control section 10 for controlling operation of the monitor, a display section 20 for displaying measured measurement data, and an input operation section 30 for use in inputting data pertinent to the measurement data. The measurement data acquired by the measurement data acquisition unit 2 are input to the control section 10 of the measurement data monitor 1.

The control section 10 controls operation of individual sections of the measurement data monitor 1 according to the data input from the measurement data acquisition unit 2 and the input operation section 30. The control section 10 has a CPU (Central Processing Unit) 11 as a principal constituent. The CPU 11 performs various numerical computing operations, information processing, and operation control in accordance with a program stored in the ROM 18. The CPU 11 uses the RAM 19 as an area for storing various sets of data.

The CPU 11 has alarm condition setup unit 12, comparison unit 13, display control unit 14, and storage unit 15. The CPU 11 acts as these units 12, 13, and 14 and perform numeral computation, information processing, and operation control.

The alarm condition setup unit 12 is configured to set conditions for giving a warning by means of an alarm. The alarm is a warning for notifying occurrence of an abnormality in the measurement data (parameter). Notification is performed by means of; for instance, a speaker sound or illumination of an indicator and by way of alarm notification unit 31.

An alarm is activated on condition that a measurement value of measured measurement data exceeds a predetermined threshold value (surpasses or falls below the threshold value) for a given period of time. A value serves as an alarm activation criterion regarding "measurement values of measurement data" is hereinbelow referred to as a threshold value. Alarm activation criteria including two elements; namely, a "threshold value for measurement data" and "duration (delay time) of the threshold value" are referred to as a setup threshold point. Activation of an alarm means that the measurement value of the measured measurement data exceeded the threshold value and that the value exceeded the threshold value continued for a predetermined period.

On the basis of a threshold point setup signal input from the input operation section 30, the alarm condition setup unit 12 performs setting setup threshold point of specified measurement data; namely, a measurement value of measurement data and duration (a delay time) of the measurement value. Incidentally, on the occasion of setting of the setup threshold point, information about the relevant measurement data that is displayed on the display section 20. A setup operator (e.g., a healthcare personnel) can set setup threshold point while referring to the data displayed on the display section 20 by way of the input operation section 30.

The comparison unit 13 is configured to compare each of sets of measurement data acquired by the measurement data acquisition unit 2 with a previously set setup threshold point of each of the sets of measurement data. As above, the setup threshold point have two elements; namely, a threshold value of the measurement data and duration (delay time) of the threshold value. Therefore, a comparison with the setup threshold point means a comparison with each of the two elements. A determination is made as to whether or not an acquired measurement value of the measurement data exceeded the previously set threshold value of the measurement data and whether or not the thus-exceeded value is measured without interruption for a previously set, given period of time. Comparison processing performed by the comparison unit 13 is performed during measurement of measurement data, and the comparison result is stored in the storage unit 15.

Some of measurement data acquired by the measurement data acquisition unit 2 may include measurement errors originating from noise or signal artifact. A determination as to whether or not the measurement errors originate from noise, or the like, is made on the basis of a signal state. A determination result is stored as measurement value reliability data, and a reference is made to the measurement value reliability data when the measurement value is plotted on a graph.

The display control unit (an example display control section) 14 is configured to control the display section 20 so as to display each of display screens including measurement data measured by the measurement data acquisition unit 2 (a calculated measurement value plot screen 21, a threshold setup screen 22, a threshold setup sub-screen 23, and the like, which will be described later) and information processed by the alarm condition setup unit 12 and the comparison unit 13.

Specifically, on the occasion of setting of the setup threshold point of the measurement data, the display control unit 14 controls the display section 20 so as to display a past calculated measurement value pertinent to the measurement data. The past calculated measurement value is displayed as a value that represents a relationship between two elements; namely, a "measurement value of measurement data" and a "duration of the measurement value."

The display control unit 14 performs control to cause the display section 20 to display, during the setting of threshold points, a setup threshold point input by way of the input operation section 30.

When setup threshold points of measurement data are set, the past calculated measurement value is displayed on the display section 20. The setup operator sets setup threshold points while making a reference to the thus-displayed, past calculated measurement value. In addition, when an attempt is made to reconfigure the once-set setup threshold point, the past calculated measurement value and an already-set, existing setup threshold point are displayed on the display section 20. The setup operator sets setup threshold points by reference to the values. Specifics to be displayed will be described in more detail by reference to FIG. 3 and FIG. 4.

Moreover, the display control unit 14 performs control for causing the display section 20 to display in real time measurement data (measurement data being measured) that are now being measured by the measurement data acquisition unit 2. Further, the display control unit 14 performs control for causing the display section 20 to display the measurement data retained in the storage unit 15.

The display control unit 14 performs control for activating an alarm on the basis of a detection result when an abnormality in measurement data is detected by comparison processing of the comparison unit 13.

The storage unit 15 stores the data generated by the measurement data acquisition unit 2, the alarm condition setup unit 12, the comparison unit 13, and the like.

Specifically, the storage unit 15 stores respective sets of past measurement data (trend data) acquired by the measurement data acquisition unit 2. Since a volume of data to be stored varies according to a type of measurement data, measurement data for several days to tens of days are stored. The storage unit 15 also stores past measurement values calculated from past measurement data.

The storage unit 15 stores a setup threshold point that will serve as an alarm activation criterion set by the alarm condition setup unit 12.

The storage unit 15 stores a comparison result acquired by the comparison unit 13. The comparison result includes a measurement value of measurement data that exceed a threshold value, duration of the measurement value, and measurement timing (a date and time), and the like.

The storage unit 15 stores data relevant to setting-related measurement data which will be displayed on the display section 20 during the setting of setup threshold points. The data include past calculated measurement values of measurement data and alarm activation data based on current setup threshold points.

The display section 20 displays on its display screen measurement data, threshold point setup data, and data relevant to the measurement data in accordance with a control signal transmitted from the display control unit 14. The display section 20 also displays the calculated measurement value plot screen 21 (an example of screen which displays the calculated measurement values on two-dimensional coordinate), the threshold setup screen 22, and the threshold setup sub-screen 23 (an example of a "histogram 24" and a "trend graph and simulated alarm display screen 25").

The calculated measurement value plot screen 21 is a display screen appearing on the display section 20 when a command (e.g., a touch on a plot reference button) for making a reference to a plot (a calculated measurement value) is input by way of the input operation section 30. The calculated measurement value plot screen 21 can display a plot (an aggregate of dots) 64 of past calculated measurement values acquired by the measurement data acquisition unit 2. In this regard, the calculated measurement value plot screen 21 is a screen for displaying calculated measurement values as two dimensional coordinate data. Display modes of the calculated measurement value plot screen 21 include a mode of displaying respective calculated measurement values as plotted dots at two dimensional coordinates, a mode of displaying the respective calculated measurement values as lines on two dimensional coordinates, and a mode of displaying the respective calculated measurement values on two dimensional coordinates and interconnecting the thus-plotted dots by lines.

Figure 2A:
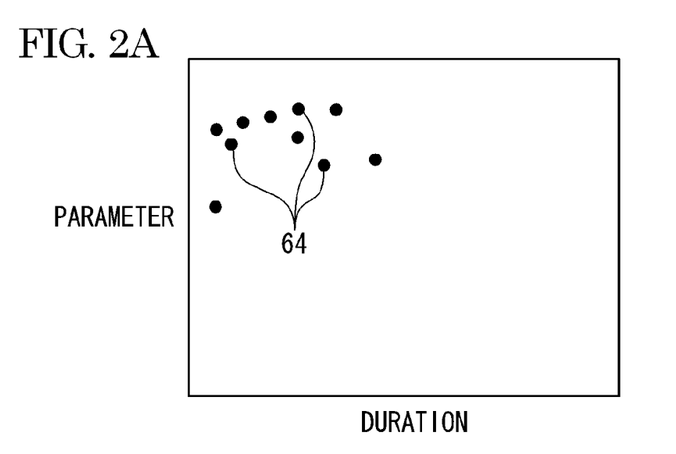
FIG. 2A is a chart illustrating an example of past calculated measurement values displayed on a calculated measurement value plot screen.

FIG. 2A indicates an example of past calculated measurement values displayed on the calculated measurement value plot screen 21. On the calculated measurement value plot screen 21, the vertical axis represents a parameter which is one of various parameters acquired by the measurement data acquisition unit 2, and the horizontal axis represents duration in which the parameter stays in a certain state. In addition to including a physiological signal or signals acquired from peripheral devices disposed around the patient; for instance, a body temperature, blood pressure, an amount of absorbed oxygen, and the like, the parameters may include one of secondary parameters resulting from measurement of the signals; for instance, a heart rate (a pulse rate), a level of oxygen in the blood, an integrated drug dosage, and the like. Further, the parameters also may include one of a cardiac output calculated from the secondary parameters, fluctuations or a rate of change in parameter, an integration, a frequency component, and the like. Moreover, the parameters also include a state determined (estimated) from a combination of the parameters; for instance, a level of low perfusion and anesthetic depth. It becomes possible for the healthcare personnel, or the like, to accurately ascertain a medical condition of an individual patient by observing the calculated measurement values displayed on the calculated measurement value plot screen 21.

The threshold setup screen 22 is a display screen that is displayed on the display section 20 when a command for setting setup threshold points is issued (e.g. a touch on the threshold setup button) by way of the input operation section 30. The threshold setup screen 22 is a screen for setting setup threshold points of measurement data (a measurement value of measurement data and its duration (a delay time)) on two dimensional coordinates. In the embodiment, a plot of past calculated measurement values of setting-related measurement data and an alarm setup threshold line (a threshold line) interconnecting setup threshold points input by way of the input operation section 30 is displayed on two-dimensional coordinates. During the setting of the setup threshold points, a mode of displaying data pertinent to past calculated measurement values of the setting-related measurement data can adopt various modes as in the case with the calculated measurement value plot screen 21. The threshold setup screen 22 can also adopt, during the setting of the setup threshold points, to receive only a threshold measurement value of measurement data and duration (a delay time) of the measurement data on two dimensional coordinates or on tabular form without displaying past calculated measurement values.

Figure 2B:
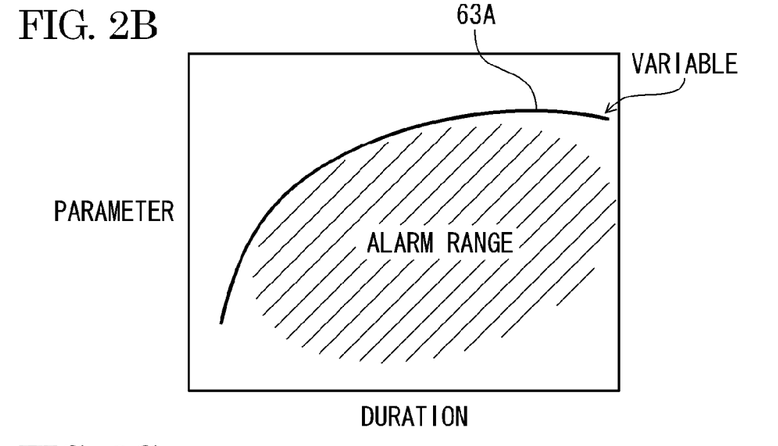
FIG. 2B is a chart illustrating an example of an alarm setup threshold line displayed on the threshold setup screen.
Figure 2C:
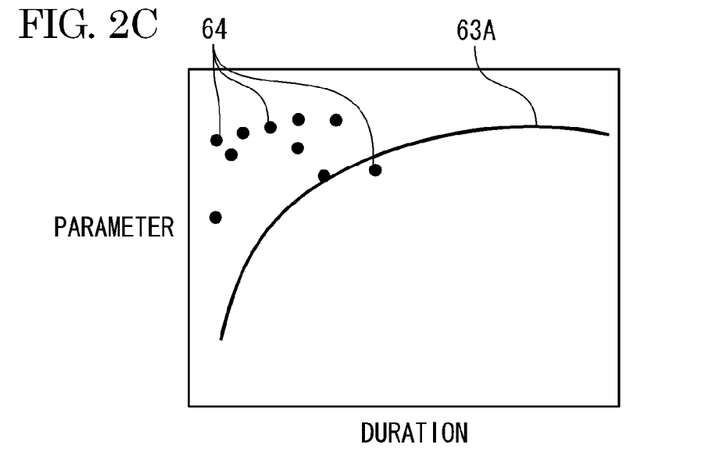
FIG. 2C is a chart that shows in an overlapping manner the calculated measurement values shown in FIG. 2A and the alarm setup threshold line.

FIG. 2B indicates an example threshold line displayed on the threshold setup screen 22. A threshold line 63A is one that becomes variable by means of a setup value input by the setup operator. A range that exceeds the line is set as an alarm range. Further, FIG. 2C indicates, in an overlapping manner, a plot (an aggregate of dots) of the past calculated measurement values shown in FIG. 2A and the threshold line shown in FIG. 2B. By comparison of the plot (an aggregate of dots) 64 with the threshold line 63A, the setup operator can determine setup threshold points more suitable for the patient. Incidentally, parameters represented by vertical axes of FIGS. 2B and 2C are the same as the parameter represented by vertical axis of FIG. 2A.

The threshold setup sub-screen 23 is a display screen that pops up on the display section 20 when a display command is provided by way of the input operation section 30 during the setting of setup threshold points. The threshold setup sub-screen 23 can display information about the measurement data relevant to the setting of setup threshold points.

For instance, when one dot in a plot of past calculated measurement values on the graph displayed on the threshold setup screen 22 is selected (e.g., the plot on the screen is touched), the threshold setup sub-screen 23 displays data relevant to the plotted dot near a point in time when the plotted dot was measured. For instance, examination data, medical record data, patient data, and the like, can be mentioned as the relevant data to be displayed. It is possible to check the reason why the dot was plotted (for example, noise), and a determination can be made as to whether or not an alarm should have been activated at the dot. Thereby, threshold points can be flexibly set.

Displaying or hiding the threshold setup sub-screen 23 can be selected in accordance with a command from the setup operator. Alternatively, displaying or hiding the threshold setup sub-screen 23 can also be arbitrarily commanded by way of the input operation section 30. Further, the threshold setup sub-screen 23 can also be displayed along with the threshold setup screen 22 as a single display screen rather than being displayed separately.

The input operation section 30 includes a keyboard, a mouse, a touch panel, and the like. The input operation section 30 is connected to the control section 10. By means of input operation, the input operation section 30 commands that the threshold setup screen 22 and the threshold setup sub-screen 23 should be displayed; selectively designates measurement data relevant to the setting of setup threshold points; and sets and inputs setup threshold points of the measurement data.

In the thus-configured measurement data monitor 1, when a signal intended for setting setup threshold points, which will be reference values of an alarm activation criterion, is input to the control section 10 by way of the input operation section 30, the display control unit 14 of the control section 10 displays the threshold setup screen 22 on the display section 20. Operation of the input operation section 30 may also be implemented by; for instance, touching a threshold setup start button displayed on the screen of the display section 20.

The display control unit 14 causes the threshold setup screen 22 to display past calculated measurement values of the setting-related measurement data of the setup threshold points designated by way of the input operation section 30. Further, when the setup threshold points are input by way of the input operation section 30, the display control unit 14 causes the threshold setup screen 22 to simultaneously display the past calculated measurement values and the setup threshold points.

By reference to the past calculated measurement values displayed on the threshold setup screen 22, the setup operator who sets setup threshold points can grasp a characteristic and a state (medical condition) of setting-related measurement data pertinent to the patient. A setup threshold point which will work as alarm activation criteria suitable for the state of the patient can thereby be set. To be specific, suitable threshold points can be set for each patient.

Figure 3:
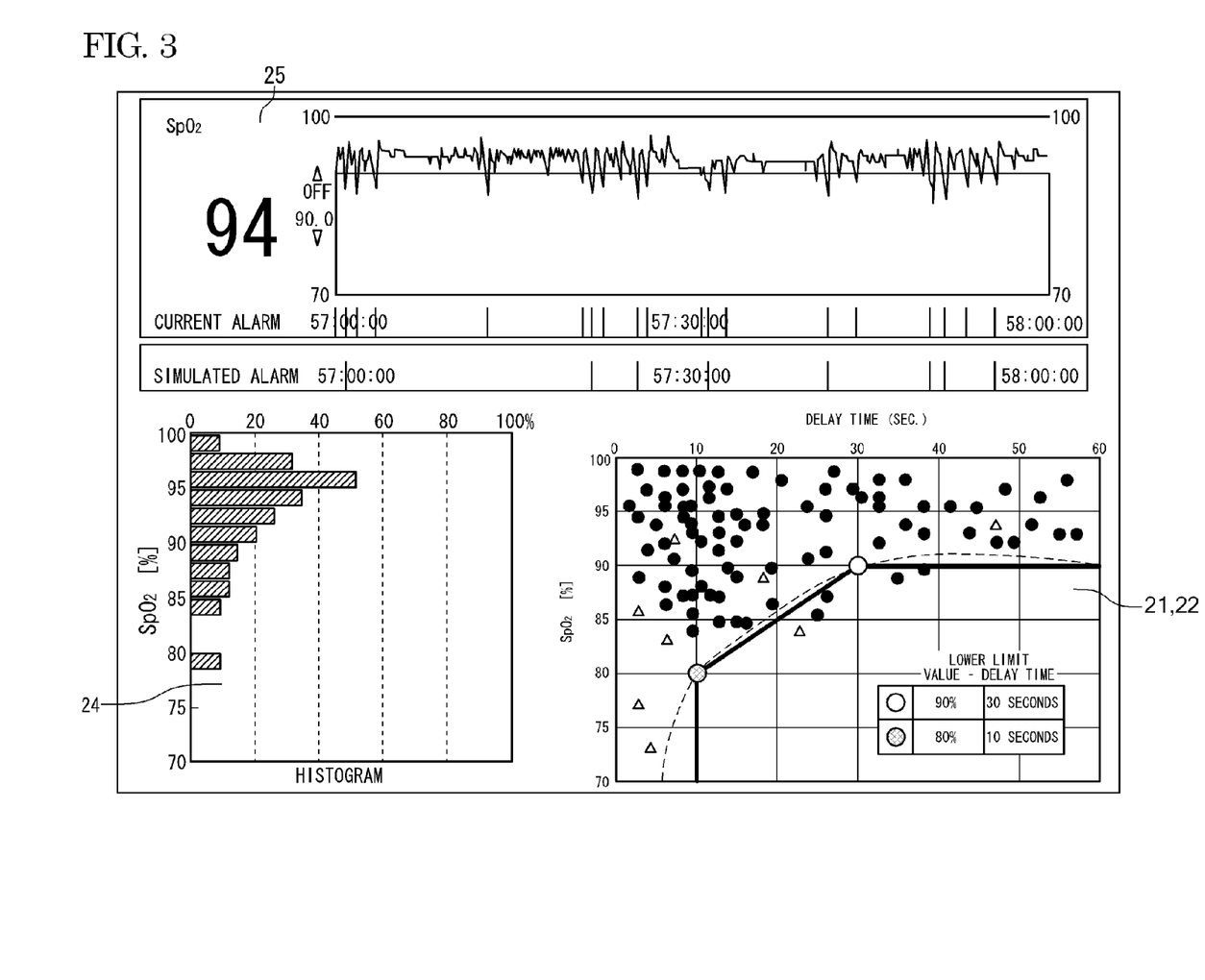
FIG. 3 is a chart illustrating an example screen that is displayed concurrently with a threshold setup screen when the alarm setup threshold line is set (changed)

FIG. 3 indicates an example of another screen displayed concurrently with the threshold setup screen 22 on the display section 20 when the threshold line is set or changed. In the embodiment, $SpO_2$ is selected as measurement data related to the setting of threshold points. The "histogram 24" and the "trend graph and simulated alarm display screen 25" are displayed as another screen (an example of the sub-screen 23) concurrently with the threshold setup screen 22 (the screen is hereunder referred to as a "general alarm setup screen"). In this regard, data to be displayed as another screen may be only the histogram 24 or the trend graph and simulated alarm display screen 25. Further, data other than those mentioned above can also be displayed.

When the setup operator operates the threshold setup start button, or the like, on the occasion of setting of the threshold line, a general alarm setup screen is displayed on the display section 20. Data pertinent to the histogram 24 are displayed on the general alarm setup screen concurrently with the threshold setup screen 22, whereby the setup operator can make a comprehensive decision in consideration of the data and set appropriate setup threshold points.

Figure 4:
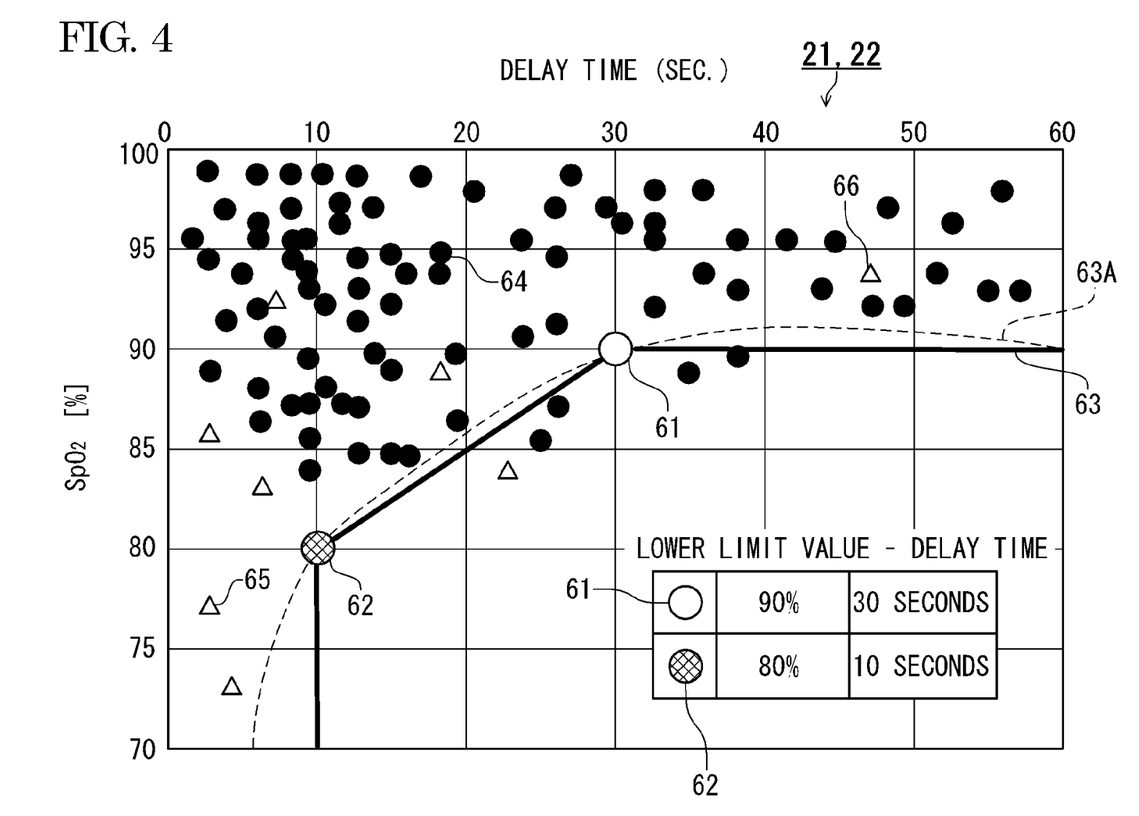
FIG. 4 is a graph illustrating a specific example of data displayed on the threshold setup screen, illustrating past calculated measurement values of measurement data and setup threshold points.

FIG. 4 illustrates in an enlarged manner the threshold setup screen 22 shown in FIG. 3.

The threshold setup screen 22 displays, as a specific example of measurement data, graphs showing the past calculated measurement values of the physiological parameter SpO$_2$ (solid circles and outlined triangles), setup threshold points 61 and 62, and a threshold line 63. The vertical axis of the graph designates SpO$_2$ [%], and the horizontal axis of the same designates a delay time (duration) [second].

Each of the setup threshold points and the past calculated measurement value include two elements; namely, a value of physiological parameter and a delay time (duration) of the value, as mentioned above. Therefore, the past calculated measurement values (solid circles) 64 show that SpO$_2$ of 95% or less was measured for about 18 seconds without interruption. The setup threshold point 61 shows that the alarm activation criterion is fulfilled when SpO$_2$ of 90% or less is measured for 30 seconds without interruption. The setup threshold point 62 shows that the alarm activation criterion is fulfilled when SpO$_2$ of 80% or less is measured for 10 seconds without interruption. The past calculated measurement values or dots along a setup boundary of the setup threshold points can also be set as "under XX %" and "greater than XX %" (under 95%, under 90%, under 80%, under 70%, and the like) by use of "under" and "greater" rather than "or more" and "or less."

In a range from 80% to 90% of SpO$_2$, the threshold line 63 determines a delay time between the SpO$_2$ values by interconnecting the setup threshold points 61 and 62 by means of a straight line, thereby determining a boundary line. In the range of under 80% of SpO$_2$, a delay time of the SpO$_2$ value is set to the same delay time as that of 80% of SpO$_2$, thereby determining the boundary line. When a calculated value is larger than 90% of SpO$_2$, the SpO$_2$ value is excluded from an alarm activation target (in other words, the value is determined to be normal), and hence no delay time is set for the SpO$_2$ value.

Past calculated measurement values (triangles) 65 and 66 include measurement errors attributable to noise and signal artifact. The past calculated measurement values are plotted on the graph as calculated measurement values that are excluded from a target of a determination as to activation of an alarm. The dots are plotted in the graph in a different shape, whereby the setup operator can visibly recognize that consideration does not need to be paid to the calculated measurement values (triangles) when setting the setup threshold points.

In FIG. 4, the number of setup threshold points to be set is set to two: the setup threshold points 61 and 62. However, the number of setup threshold points to be set is not limited to two. The threshold line 63 can also be set by setting three setup threshold points or more. Further, the threshold line 63 is displayed as a straight line in FIG. 4 but not limited to this form. The threshold line can also be displayed by means of a quadratic curve 63A which is plotted by use of a plurality of setup threshold points (e.g., the setup threshold points 61 and 62, and the like) by means of curve approximation, or the like.

By reference to the past calculated measurement values, the causes of the alarms occurred in the past, a necessity for the alarms, the current state of the patient, and others, a plurality of (at least two) setup threshold points are set in detail, whereby alarm activation criteria optimum for the patient can be set.

An area on the graph where the plotted dots congregate shows that the calculated measurement values (measurement values and their durations) have frequently occurred in the patient up to this. Therefore, if the patient is determined to be normal from the calculated measurement values, the threshold line 63 can be determined so as to avoid the plotted dots.

When the past calculated measurement values are displayed on the graph, the plotted dots can also be displayed in different colors according to a time zone where the calculated measurement values were acquired. Namely, a color of a plotted dot can also be changed according to whether the calculated measurement value was acquired in the morning, in the daytime, and in the night time.

In addition, plotted dots where an abnormality did not occur in the patient and plotted dots at which an abnormality occurred in the patient can be displayed on the graph in different colors, respectively. The setup operator can set setup threshold points while visually checking plotted dots such that plotted dots where an abnormality occurred are not put outside the threshold line; namely, such that an alarm is activated without fail by means of calculated measurement values of the plotted dots. Accordingly, setup threshold points more appropriate for the patient can be readily set.

Figure 5:
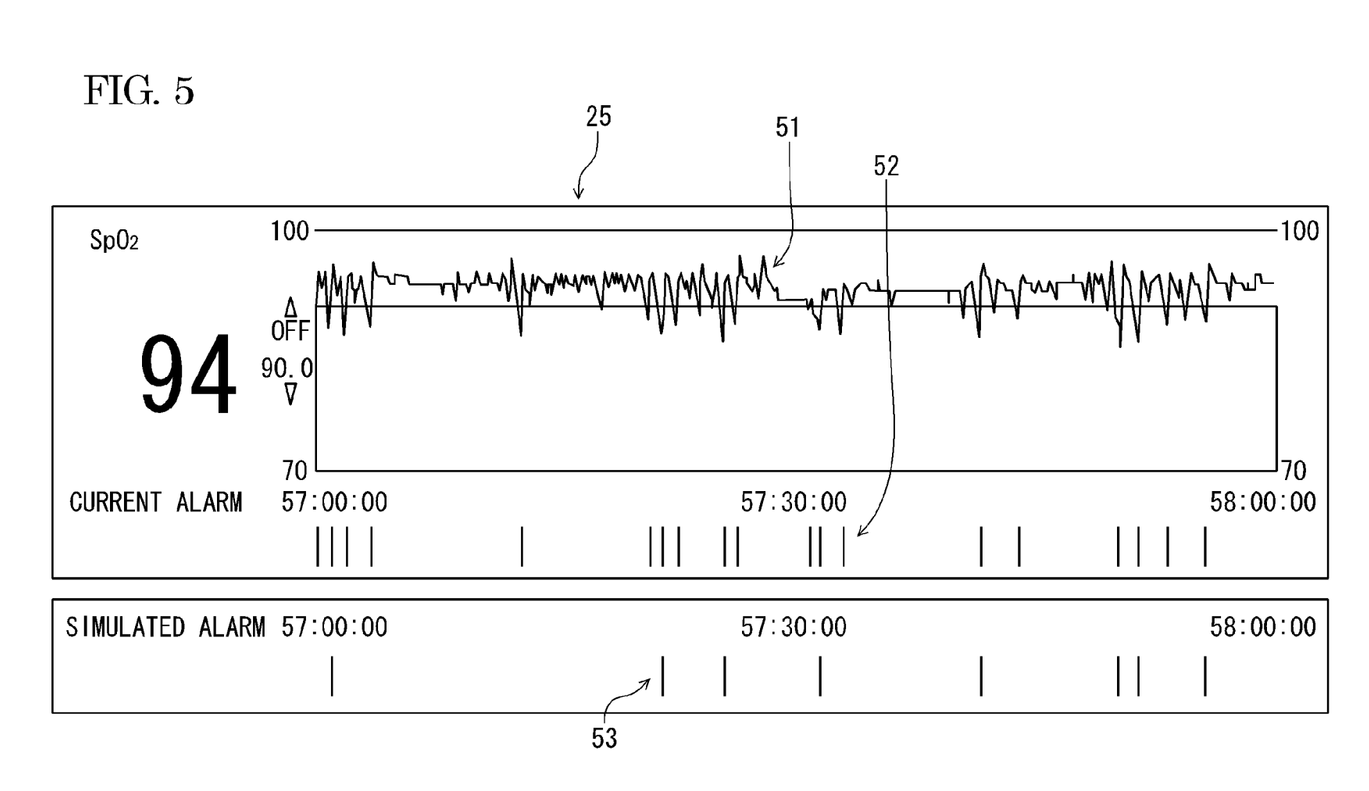
FIG. 5 is a chart illustrating a specific example of data displayed on the threshold setup screen, illustrating alarm activation data caused by existing threshold line and alarm activation simulation data simulated by new setup threshold line.

FIG. 5 indicates a trend graph and the simulated alarm display screen 25 that are displayed simultaneously with the threshold setup screen 22 on the general alarm setup screen shown in FIG. 3.

The drawing shows measurement data 51 that are obtained during a predetermined period of physiological parameter pertinent to the setup threshold point, data 52 (also called alarm activation data) pertinent to timing at which an alarm is activated with regard to the measurement data 51 based on the setup threshold points at the time the alarm activated, and alarm activation simulation data 53 that are simulated to activate an alarm for the measurement data 51 if the setup threshold points are newly changed setup points.

As above, the alarm activation simulation data 53 are contrastingly displayed on the same screen that is now displaying the past measured data 51 and the alarm activation timing data 52 based on the setup threshold points at the time the alarm activated whereby the setup operator can recognize in detail a relationship between alarms which will be activated by the new setup threshold points and the measurement data. The above contrast display function may be called a simulated alarm display function.

Procedures for calculating the past calculated measurement values are now described.

Figure 6A:
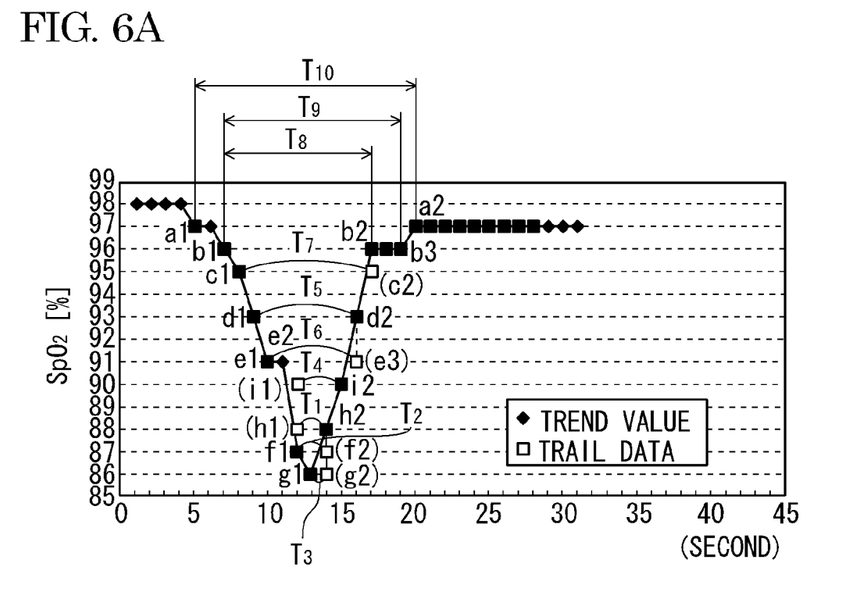
FIG. 6A is a graph illustrating a change in measurement values of $SpO_2$.
Figure 6B:
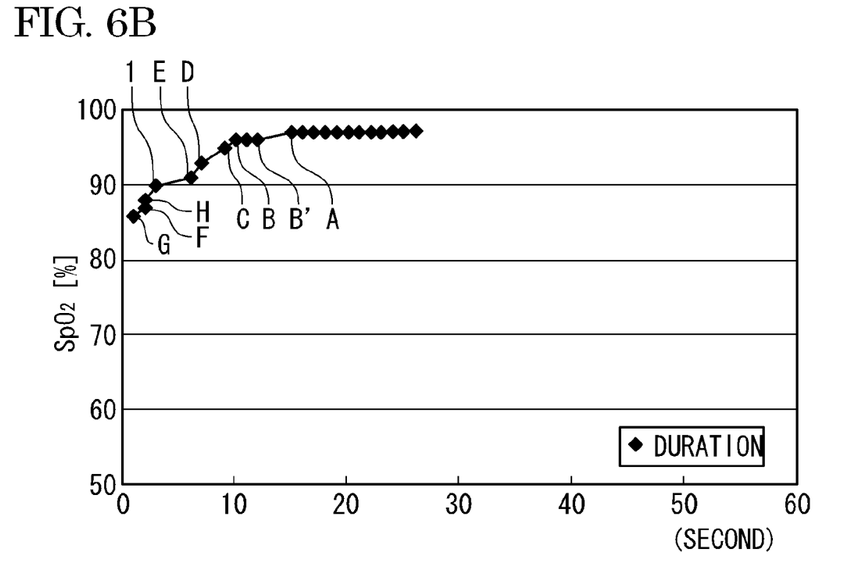
FIG. 6B is a graph illustrating a plot of duration of measured $SpO_2$ values.

FIGS. 6A and 6B are graphs for explaining procedures for calculating past calculated measurement values of physiological parameter SpO$_2$.

FIG. 6A is a graph that plots a measured SpO$_2$ value on a per-second basis. Measurement values show a change in a direction in which the values decrement (an outward direction) and subsequently show another change in a direction in which the measurement values increment (an inward direction), thereby creating one valley (event).

In order to calculate measurement values from the graph, calculation of measurement values is not conducted in a period during which the measurement values change in a decrementing direction (i.e., a period during which a change occurs in sequence of a1→b1→c1→d1→e1→f1→g1). Calculation of measurement values is conducted in a period during which the measurement values change in an incrementing direction (i.e., a period during which a change occurs in sequence of h2→i2→d2→b2→b3→a2).

Specifically, in the case of dot "h," attention is paid to dot "h2" in a period during which the measurement values change in the incrementing direction. When there is performed a search for a dot at which a measurement value exceeds 88% and which precedes dot "h2," dot "e2" is detected. Specifically, a value measured at dot "f1" is 88% or less, but a value measured at dot "e2" immediately preceding dot "f1" exceeds 88%. Accordingly, duration of the value of 88% or less is obtained by measuring a time of period T1 between f1 (h1) and h2, and there is obtained T1=2 seconds. A measurement value showing that a measurement value of 88% or less continued two seconds is thereby calculated.

In the example shown in FIG. 6A, dot "e2" is determined as a result of performance of a search for a dot where a measurement value exceeds 88% that is a value measured at h2. In the example, dot "f1" (87%) and dot "g1" (86%) were measured in an area between dot "e2" and dot "h2." At a point in time when dot "h2" is obtained, there are determined duration of a calculated measurement value that is smaller than the value measured at dot "f1" and duration of a calculated measurement value that is smaller than the value measured at dot "g1." For instance, in the case of dot "f," since a value measured in an area from dot "f1" to a point immediately before dot "h2" is 87% or less, the duration corresponds to a period T2 between "f1" and "h2 (f2)"=2 seconds.

Likewise, in the case of dot "g," a value measured in an area from dot "g1" to dot "h2" is 86% or less, duration of the calculation value corresponds to period T3 between "g1" and "h2 (g2)"=one second.

Similarly, in the case of dot "i," a period T4 between (i1) and "i2"=three seconds is determined from (i1) that is timing subsequent to dot "e2" (a measurement value of 91%) and dot "i2" (90%). A measurement value showing that a measurement value of 90% or less continued for three seconds is thereby calculated.

In the case of dot "d," a period T5 between "d1" and "d2"=seven seconds is similarly determined from dot "d1" (a measurement value of 93%) and dot "d2" (a measurement value of 93%). A measurement value showing that a measurement value of 93% or less continued for seven seconds is thereby calculated.

In the case of dot "e," dot (e3) is determined at a point in time when dot "d2" (a measurement value of 93%) is obtained, whereby a period T6 between "e1" and (e3)=six seconds is obtained. A measurement value showing that a measurement value of 91% or less continued for six seconds is thereby calculated.

Likewise, in the case of dot "c," dot (c2) is determined at a point in time when dot "b2" (a measurement value of 96%) is obtained, whereby a period T7 between "c1" and (c2)= nine seconds is obtained. A measurement value showing that a measurement value of 95% or less continued for nine seconds is thereby calculated.

In the case of dot "b," a period T8 between "b1" and "b2"=10 seconds and a period T9 between "b1" and "b3"=12 seconds are likewise determined from dots "b1," "b2," and "b3" (a measurement value of 96%). A measurement value showing that a measurement value of 96% continued for 10 seconds and a measurement value showing that a measurement value of 96% continued for 12 seconds are thereby calculated.

In the case of dot "a," a period T10 between "a1" and "a2"=15 seconds is determined from dot "a1" and dot "a2" (a measurement value of 97%). A measurement value showing that a measurement value of 97% continued for 15 seconds is thereby calculated.

FIG. 6B is a graph that plots respective measurement values calculated from the graph shown in FIG. 6A and that shows interconnected plots.

Point G is a calculated measurement value pertinent to dot "g" and includes elements showing that physiological parameter assume a value of 86% and that the measurement value continued for one second. Point F is a calculated measurement value pertinent to dot "f" and includes elements showing that physiological parameter assume a value of 87% and that the measurement value continued for two seconds. Point H is a calculated measurement value pertinent to dot "h" and includes elements showing that physiological parameter assume a value of 88% and that the measurement value continued for two seconds. Point I is a calculated measurement value pertinent to dot "i" and includes elements showing that physiological parameter assume a value of 90% and that the measurement value continued for three seconds. Point E is a calculated measurement value pertinent to dot "e" and includes elements showing that physiological parameter assume a value of 91% and that the measurement value continued for six seconds. Point D is a calculated measurement value pertinent to dot "d" and includes elements showing that physiological parameter assume a value of 93% and that the measurement value continued for seven seconds. Point C is a calculated measurement value pertinent to dot "c" and includes elements showing that physiological parameter assume a value of 95% and that the measurement value continued for nine seconds. Points B and B' correspond to calculated measurement values pertinent to dots "b" and include elements showing that physiological parameter assume a value of 96% and that the measurement value continued for 10 seconds, as well as showing that physiological parameter assume a value of 96% and that the measurement value continued for 12 seconds. Point A is a calculated measurement value pertinent to dot "a" and includes elements showing that physiological parameter assume a value of 97% and that the measurement value continued for 15 seconds.

The thus-calculated measurement values are plotted as past calculated measurement values on; for instance, the calculated measurement value plot screen 21 or a graph of the threshold setup screen 22 illustrated in FIGS. 3 and 4. The calculated measurement values are used as data for determining a medical state of the patient or reference data at the time of setting of the setup threshold points.

The plot (an aggregate of dots) of the calculated measurement values generates a plurality of dots for one event (e.g., a drop in $SpO_2$). The dots can also be categorized in terms of a given preset standard, and only dots conforming to the standard can be displayed in a different form. For instance, measurement values calculated in connection with dot "g1" in one valley that is formed from measurement values (FIG. 6A) can also be displayed on a graph as a set of data by interconnecting the calculated measurement values. The individual event can thereby be ascertained.

Figure 7:
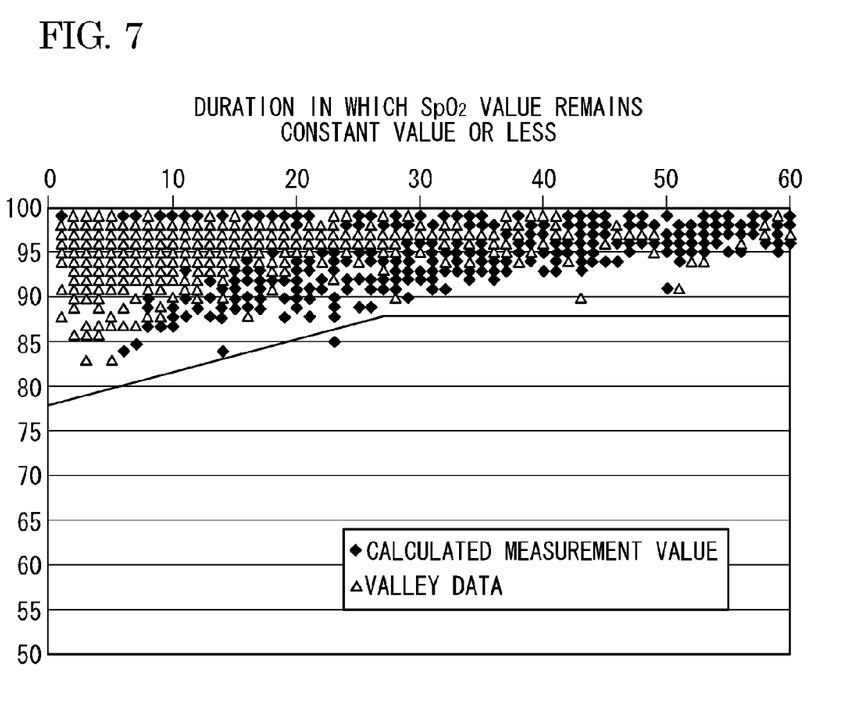
FIG. 7 is a graph illustrating a specific example illustrating that only dots conforming to predetermined standards, among the calculated measurement values, are displayed in different modes.

In addition, in this case, only the data pertaining to a peak (a valley or a crest) can be displayed in a changed plot shape (or plot color). This facilitates grasping the number of events and allows recognition of the number of times an alarm was activated, whereby more flexible setting of a threshold value becomes feasible. Moreover, only data that exhibit a low level of reliability and that are based on reliability data pertaining to measurement values determined by the measurement data acquisition unit 2 may be displayed in a different plot format (a shape, a color, or the like). Further, patient data measured in the morning, the daytime, and the night can also be displayed in different plot forms, respectively. This enables easy recognition of specifics of calculated measurement values and prompt and accurate performance of determination.

In the examples, explanations have been given to the procedures for calculating past calculated measurement values by use of the valley-shaped data shown in FIGS. 6A and 6B. However, calculation can be performed in the same manner even when mountain-shaped data are used. For instance, when mountain-shaped data are used, a direction in which measurement values increment is taken as an outward change, whilst a direction in which measurement values decrement is taken as an inward change. In other respects, all you have to do is to calculate the past measurement values as in the case with the above example.

Figure 8:
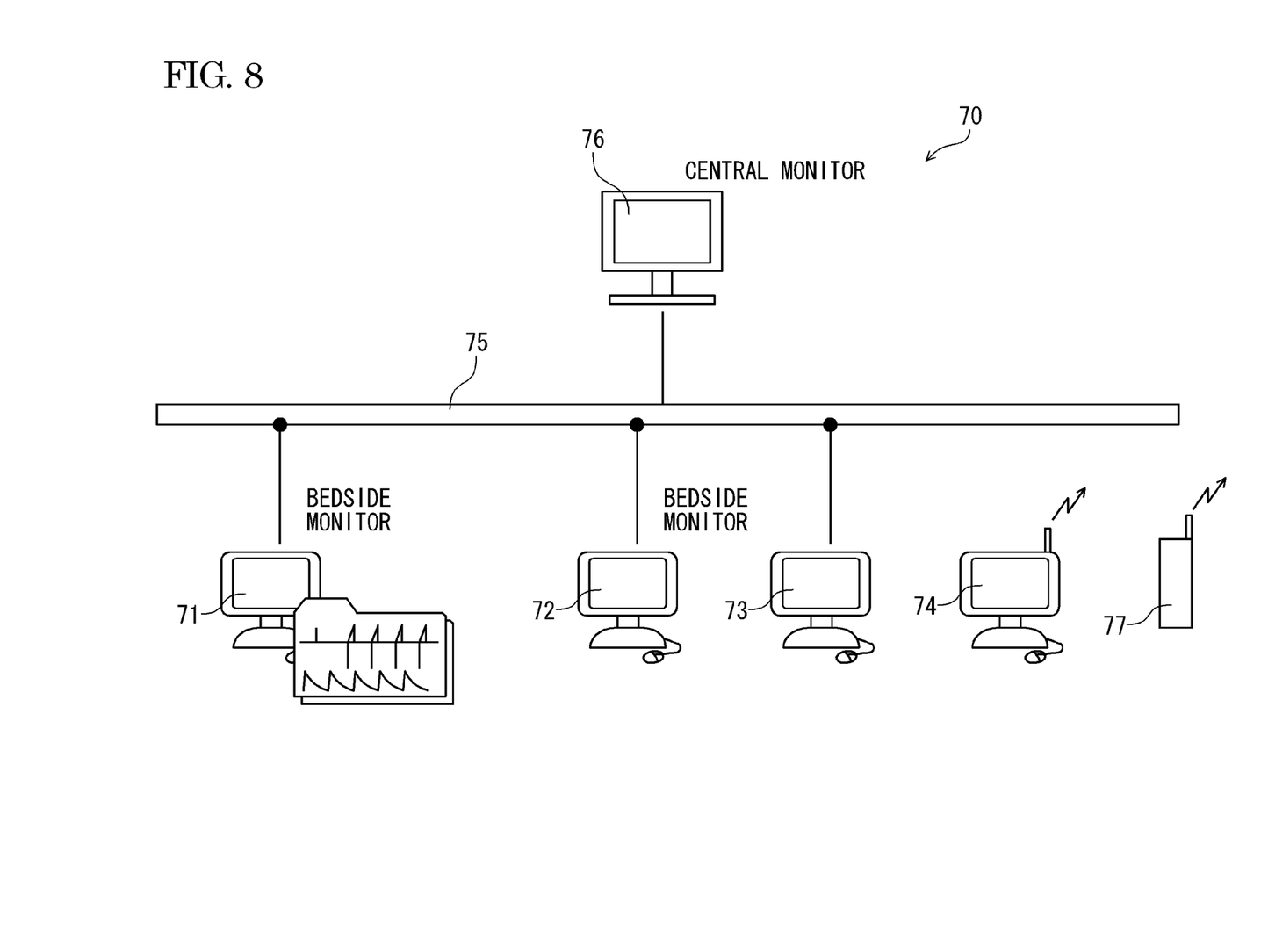
FIG. 8 is a drawing illustrating a mode of a measurement data monitoring system for medical equipment connected via a network.

FIG. 8 illustrates a measurement data monitoring system for medical equipment 70 made up of a plurality of measurement data monitors (bedside monitors) 71, 72, and 73, a transmitter-equipped monitor 74, a transmitter 77, and a central monitor 76 that are interconnected via a network 75. In this regard, the measurement data monitoring system for medical equipment 70 can be devoid of some of the bedside monitors 71, 72, 73, the transmitter-equipped monitor 74, and the transmitter 77. The measurement data monitoring system may include a plural number of the bedside monitors 71, 72, 73, the transmitter-equipped monitor 74, or the transmitter 77. Various combinations of the bedside monitors 71, 72, 73, the transmitter-equipped monitor 74, and the transmitter 77 can be adapted to the measurement data monitoring system.

The central monitor 76 is a monitor that is disposed in a medical staff room, and the like, to allow centralized monitoring of measurement data pertinent to patients. In addition to the measurement data measured by the respective measurement data monitors 71, 72, and 73 and the measured past measurement values, all data that can be displayed on the respective measurement data monitors 71, 72, and 73 (identical with data that can be displayed by the aforementioned measurement data monitor 1) are transmitted to the central monitor 76 via the network 75. Data similar to those transmitted from the respective measurement data monitors 71, 72, and 73 are also wirelessly transmitted even from the transmitter-equipped monitor 74. A transmitter 77 wirelessly transmits to the central monitor 76 the measurement data measured by the transmitter 77. The thus-transmitted data are retained in a memory section of the central monitor 76.

In addition to being able to display data that are the same as those displayed on the respective measurement data monitors 71, 72, and 73 and the transmitter-equipped monitor 74, the display screen of the central monitor 76 can simultaneously display data pertinent to a plurality of patients measured by the plurality of measurement data monitors. For instance, a plot of calculated measurement values (an aggregate of dots) pertaining to a plurality of patients can be displayed side by side in respective split views on the display screen. Alternatively, a plot of calculated measurement values (an aggregate of dots) pertaining to a plurality of patients can be displayed while overlapping plots in the same view of the same display screen. Such a display can be provided for each facility of a hospital (like a per-site basis), such as a hospital ward or for each of diseases of patients. An alarm trend can thereby be checked. Further, a unique plot of dots can be detected from among the overlaid plots. The patient of the unique measurement data can be specified by selection of plotted dots, whereby appropriate threshold points can be set flexibly.

The configuration described in connection with the embodiment enables the healthcare personnel to grasp a characteristic of relevant measurement data; namely, data pertinent to the patient and the patient's status (medical condition), by reference to values being measured or past calculated measurement values that are displayed on the calculated measurement value plot screen 21. The healthcare personnel can thereby take measures appropriate for the patient's status.

By reference to the values being measured or the past calculated measurement values displayed on the threshold setup screen 22, the setup operator who sets threshold points can grasp a characteristic of relevant measurement data; namely, data pertinent to the patient and the patient's status (medical condition), by reference to the values being measured or the past calculated measurement values that are displayed on the calculated measurement value plot screen 21. A feeling of anxiety that arises in the setup operator who sets threshold points; namely, anxiety that safety can be surely assured, is thereby lessened, and setup threshold line that will serve as the alarm activation criteria appropriate for the status of the patient can be set. Specifically, setup threshold line appropriate for each patient can be set. Accordingly, the number of times an unwanted alarm is activated can also be diminished. Further, data pertinent to duration of a certain value of medical data being measured is included in the past calculated measurement values to be displayed on the screen, whereby the setup operator (the healthcare personnel) can readily perform operation for setting threshold line of the medical data at will.

Since the graph including the threshold line 63 is displayed on the threshold setup screen 22, the setup operator can readily set setup threshold points while visually referring to the calculated measurement values plotted on the graph.

The threshold boundary line 63 is formed from at least two setup threshold points or more. For this reason, the setup operator who sets threshold points can set setup threshold points by reference to a plurality of factors, like a current status of the patient. Thus, alarm activation criteria optimum for the patient can be set.

The alarm activation simulation data 53 can be contrastingly displayed on the same screen where is displaying the past measurement data 51 and the alarm activation timing data 52 based on the setup threshold points at the time the alarm activated. A relationship between an alarm which will be activated by new setup threshold points and measurement data can be recognized in detail.

The trend graph and the histogram 24 of relevant measurement data are displayed on the display section 20 concurrently with the past calculated measurement values, whereby suitable setup threshold points can be set on the basis of relevant data. Thus, alarm activation criteria optimum for the patient can be set.

Plotted dots conforming to a predetermined standard of the calculated measurement values are displayed in different forms (shapes or colors), thereby enabling easy ascertainment of the quality of physiological parameter and the number of events. Thus, threshold points can be set more flexibly.

As a result of selection of one of plotted dots of calculated measurement values, data relevant to the plotted dot are displayed. Accordingly, accuracy of the setting of threshold points can be enhanced qualitatively by reference to the relevant data.

Plots of calculated measurement values of a plurality of patients are displayed, while being overlaid, on the central monitor 76 connected to the network, whereby an alarm trend of patients can be readily checked on a per-facility basis or a per-disease basis. Moreover, a unique plotted dot can be readily detected.

The presently disclosed subject matter is not limited to the monitor and the monitoring system exemplified in connection with the embodiment and susceptible to alterations as needed without departing the gist of the presently disclosed subject matter.

According to the presently disclosed subject matter, when determining a medical condition of a patient, the healthcare personnel can make an accurate determination about a medical condition in agreement with a state of the patient by observing a calculated measurement value including elements; namely, a measurement value of measurement data and duration of the measurement value. Further, at the time of setting of setup threshold points, the setup threshold points can be set by use of a threshold setup screen for setting setup threshold line of measurement data. Accordingly, optimum setup threshold points conforming to the state of the patient can be set.

What is claimed is:

1. A measurement data monitor for medical equipment comprising:
    a display section configured to display measurement data measured by the medical equipment;
    a display control section configured to cause the display section to display the measurement data,
    wherein the measurement data displayed on the display section include calculated measurement values that contain elements of the measurement data and of a duration that the measurement data exceeded a given threshold,
    wherein the display control section displays the measurement data on a two-dimensional coordinate plane including a measurement data axis and a duration axis on the display section, such that a duration axis coordinate of the displayed measurement data indicates a length of time in which the measurement data exceeded the given threshold,
    wherein the display control section displays a threshold setup screen on the display section that is used for setting, on the two-dimensional coordinate plane, threshold points of the measurement data that are to serve as criteria for determining activation of an alarm,
    wherein the calculated measurement values are displayed as two-dimensional coordinate data on the threshold setup screen at the time of setting of the threshold points, and
    wherein the threshold points, each of which include two elements including a threshold value for the measurement data and duration of the measurement value, are displayed on the threshold setup screen to form a threshold line.

2. The measurement data monitor for medical equipment according to claim 1, wherein the measurement data displayed on the display section include calculated measurement values that were measured in the past.

3. The measurement data monitor for medical equipment according to claim 1, wherein the threshold line is formed based on at least two threshold points.

4. The measurement data monitor for medical equipment according to claim 1, wherein the display section displays at least one of a trend graph and a histogram of relevant measurement data.

5. The measurement data monitor for medical equipment according to claim 1, wherein the display section displays the measurement data, alarm activation data that are caused by existing setup threshold value set with regard to the measurement data, and alarm activation simulation data that are simulated to be caused by threshold points changed and set with regard to the measurement data.

6. The measurement data monitor for medical equipment according to claim 1, wherein dots to be plotted on the graph are categorized according to a predetermined standard, and plotted dots conforming to the standard are displayed in different forms.

7. The measurement data monitor for medical equipment according to claim 1, wherein dots plotted on the graph where the calculated measurement values are displayed is selected, whereby relevant data near a point in time when the plotted dot was measured are displayed.

8. The measurement data monitor for medical equipment according to claim 1, wherein dots to be plotted on the graph are categorized according to a predetermined standard, and plotted dots conforming to the standard are displayed in different forms.

9. The measurement data monitor for medical equipment according to claim 1, wherein dots plotted on the graph where the calculated measurement values are displayed is selected, whereby relevant data near a point in time when the plotted dot was measured are displayed.

10. A measurement data monitor for medical equipment comprising:
    a display section; and
    a display control section configured to control the display section,
    wherein the display control section displays a threshold setup screen on the display section that is used for setting threshold points used as criteria for determining activation of an alarm in a format which is specified by a measurement value of measurement data measured by medical equipment and a delay time of the measurement value,
    wherein the measurement data displayed on the display section include calculated measurement values that contain elements of the measurement data and of a duration that the measurement data exceeded a given threshold,
    wherein the display control section displays the measurement data on a two-dimensional coordinate plane including a measurement data axis and a duration axis on the display section, such that a duration axis coordinate of the displayed measurement data indicates a length of time in which the measurement data exceeded the given threshold,
    wherein the calculated measurement values are displayed as two-dimensional coordinate data on the threshold setup screen at the time of setting of the threshold points, and
    wherein the threshold points, each of which include two elements including a threshold value for the measurement data and duration of the measurement value, are displayed on the threshold setup screen to form a threshold line.

11. A measurement data monitoring system for medical equipment that includes a plurality of measurement data monitors for medical equipment and a central monitor which manages the monitors in a centralized manner and which is connected to the monitors via a network, and that is operable to display calculated measurement values of various parameters acquired by a respective measurement data monitors on the central monitor via the network, wherein calculated measurement values of a plurality of patients are plotted and displayed, while being overlaid, on the central monitor, wherein the measurement data displayed includes calculated measurement values that contain elements of the measurement data and of a duration that the measurement data exceeded a given threshold, wherein the measurement data is displayed on a two-dimensional coordinate plane including a measurement data axis and a duration axis, such that a duration axis coordinate of the displayed measurement data indicates a length of time in which the measurement data exceeded the given threshold wherein a threshold setup screen is displayed for setting, on the two-dimensional coordinate plane, threshold points of the measurement data that are to serve as criteria for determining activation of an alarm, wherein the calculated measurement values are displayed as two-dimensional coordinate data on the threshold setup screen at the time of setting of the threshold points, and wherein the threshold points, each of which include two elements including a threshold value for the measurement data and duration of the measurement value, are displayed on the threshold setup screen to form a threshold line.

* * * * *